United States Patent [19]

Byram et al.

[11] Patent Number: 5,716,607
[45] Date of Patent: *Feb. 10, 1998

[54] METHODS TO INHIBIT LATE RADIATION-INDUCED SKIN DAMAGE

[75] Inventors: Michael M. Byram, Colorado Springs, Colo.; Robert Goebel, Huntington Beach, Calif.; Richard J. Greff, St. Petersburg, Fla.; Leonard V. Barley, Jr., Colorado Springs, Colo.

[73] Assignee: MedLogic Global Corporation, Colorado Springs, Colo.

[*] Notice: The term of this patent shall not extend beyond the expiration date of Pat. No. 5,554,365.

[21] Appl. No.: 643,400

[22] Filed: May 6, 1996

Related U.S. Application Data

[63] Continuation-in-part of Ser. No. 435,590, May 5, 1995, Pat. No. 5,554,365.

[51] Int. Cl.⁶ .......................... A61K 31/74; A61K 31/78
[52] U.S. Cl. .......................... 424/78.02; 514/528
[58] Field of Search .......................... 424/78.02; 514/528

[56] References Cited

U.S. PATENT DOCUMENTS

| | | |
|---|---|---|
| 3,722,599 | 3/1973 | Robertson et al. |
| 4,737,544 | 4/1988 | McCain et al. ............... 525/54.1 |
| 5,254,132 | 10/1993 | Barley et al. |
| 5,306,490 | 4/1994 | Barley et al. |
| 5,403,591 | 4/1995 | Tighe et al. |
| 5,554,365 | 9/1996 | Byram et al. ............... 424/78.02 |

FOREIGN PATENT DOCUMENTS

93/25196  12/1993  WIPO.

OTHER PUBLICATIONS

Sitton, *Early and Late Radiation–Induced Skin Alterations Part I:Mechanisms of Skin Changes*, Oncology Nursing Forum, 19(5):801–807 (1992).
Sitton, *Early and Late Radiation–Induced Skin Alterations Part II:Nursing Care of Irradiated Skin*, Oncology Nursing Forum, 19(6):907–912 (1992).
Dini, et al., *Management of Acute Radiodermatit's*, Cancer Nursing, 16(5):366–370 (1993).
Perez, et al., *Principles and Practice of Radiation Oncology*, Second Edition, J.B. Lippincott Company, Philadelphia, PA, pp. 104–105 (1987).
Rubin et al., *Skin and Adnexa*, Clinical Radiation and Pathology, Chapter 3, pp. 62–119 (1986).

Primary Examiner—Joseph L. Schofer
Assistant Examiner—Wu C. Cheng

[57] ABSTRACT

Disclosed are methods for inhibiting late radiation-induced skin damage during treatment of a patient with ionizing radiation by application of a layer of biocompatible polymer to the skin surface prior to exposure of the surface to ionizing radiation.

31 Claims, No Drawings

METHODS TO INHIBIT LATE RADIATION-INDUCED SKIN DAMAGE

CROSS-REFERENCE TO RELATED APPLICATIONS

This application is a continuation-in-part of U.S. patent application Ser. No. 08/435,590, filed May 5, 1995, now U.S. Pat. No. 5,554,365, which application is incorporated herein by reference in its entirety.

BACKGROUND OF THE INVENTION

1. Field of the Invention

This invention is directed to methods for inhibiting late radiation-induced skin damage arising after treatment of a patient with ionizing radiation. Specifically, the methods of this invention involve formation of a layer of biocompatible polymer over the skin surface prior to exposure of the surface to ionizing radiation.

In one embodiment, the biocompatible polymer layer can be formed by solvent casting or by the in situ polymer formation on the skin surface.

References

The following publications, patent applications and patents are cited in this application as superscript numbers:

1. Sitton, *"Early and Late Radiation-Induced Skin Alterations Part I:Mechanisms of Skin Changes"*, Oncology Nursing Forum, 19(5):801–807 (1992)
2. Sitton, *"Early and Late Radiation-Induced Skin Alterations Part II:Nursing Care of irradiated Skin"*, Oncology Nursing Forum, 19(6):907–912 (1992)
3. Dini, et al., *"Management of Acute Radiodermatitis"*, Cancer Nursing, 16(5):366–370 (1993)
4. Barley, *"Methods for Retarding Blister Formation by Use of Cyanoacrylate Adhesives"*, U.S. Pat. No. 5,306,490, issued Apr. 26, 1994.
5. Tighe, et al., U.S. Pat. No. 5,580,565, for *Use of Cyanoacrylates for Providing a Protective Barrier*, issued on Dec. 3, 1996.
6. Perez, et al., *Principles and Practice of Radiation Oncology*, Second Edition, J.B. Lippincott Company, Philadelphia, Pa., pp. 104–105 (1987)
7. Barley, et al., *Methods for Treating Suturable Wounds by Use of Sutures and Cyanoacrylate Adhesives*, U.S. Pat. No. 5,254,132, issued Oct. 19, 1993
8. Robertson, et al., *Fluorocyanoacrylates*, U.S. Pat. No. 3,722,599, issued Mar. 27, 1973
9. Barley, et al., International Patent Application Publication No. WO 93/25196, for *Methods for Treating Non-Suturable Wounds by Use of Cyanoacrylate Adhesives*, published Dec. 23, 1993
10. Barley, et al., U.S. Pat. No. 5,653,769, for *Methods for Reducing Skin Irritation From Artificial Devices by Use of Cyanoacrylate Adhesives*, issued on Aug. 5, 1997
11. Tighe, et al., U.S. Pat. No. 5,403,591, for *Methods for Inhibiting Skin Ulceration by Use of Cyanoacrylate Adhesives* issued Apr. 4, 1995
12. Rubin, et al., *Clinical Radiation and Pathology*, Chapter 3, Skin and Adnexa, pp. 62–119 (1986)

All of the above publications, patent applications and patents are herein incorporated by reference in their entirety to the same extent as if each individual publication, patent application or patent was specifically and individually indicated to be incorporated by reference in its entirety.

2. State of the Art

Treatment regimens for many tumors (e.g., tumors of the head, neck, chest, breasts, prostate, etc.) currently include daily exposure of the tumor to ionizing radiation repeated over a period of time where application of the radiation to the site of the tumor is through the skin.[1] Typical regimens include daily (e.g., five times per week) exposure of the tumor with ionizing radiation for about 5 or more weeks wherein both the length of treatment and the total dosage of radiation are dictated by the tumor size, location, etc. For example, treatment regimens for small microscopic tumors typically include daily exposure of the tumor to ionizing radiation for approximately 5 weeks with a cumulative ionizing radiation dosage of about 4500–5000 rads [45–50 Gray (Gy)]. Treatment regimens for larger tumors as well as tumors located in the head and neck typically are extended to 8 or more weeks and can employ a cumulative ionizing radiation dosage of about 7400 or more rads (74 or more Gy). Treatment of tumors located in the head and neck are particularly troublesome because stem cells associated with such tumors will exhibit maximal recruitment of tumor cells approximately half way through the treatment schedule. To compensate for this recruitment, there is some interest in hyperfractionation of the ionizing radiation where the radiation is applied more than once daily to the patient. Hyperfractionation requires, however, that acute radiation-induced skin damage be within tolerable limits during the treatment regimen.[6]

Notwithstanding the benefits of ionizing radiation in the treatment of many tumors, late radiation-induced skin injuries, such as atrophy, thinning of the skin, telangiectasia, altered pigmentation, fibrosis, ulceration, necrosis and carcinogenesis, occurs about 6 or more months after treatment with ionizing radiation[12]. Such late radiation-induced skin injuries are related to vascular and connective changes arising from exposure to ionizing radiation[1].

Heretofore, the art has addressed acute radiation-induced skin damage by use of ointments, lotions, powders, occlusive dressings, etc. on the damaged skin[1,2]. Likewise, Dini, et at.[3] discloses the use of a foam emulsion containing hydrophilic (propylene glycol, glycerol and polyunsaturated alcohols) and hydrophobic (stearic acid) components which was applied to radiation-induced damaged skin in order to enhance recovery of the damaged skin. There has, however, been little published information on inhibition of late radiation-induced skin damage.

It is apparent, then, that there is a continuing need in the art of radiation oncology to inhibit the degree of skin damage induced months after exposure to ionizing radiation.

This invention is directed, in part, to the discovery that formation of a biocompatible polymer layer over the surface of the skin area which is to be exposed to ionizing radiation followed by exposure to ionizing radiation through this layer reduces the degree of late radiation-induced skin damage in the patient.

The biocompatible polymer layer is preferably formed by solvent casting or by the in situ polymer formation on the skin surface. When in situ polymerization is employed, a reactive monomer or oligomer (i.e., prepolymer) is applied onto the skin which, in situ, polymerizes to form the polymer layer. A particularly preferred reactive monomer or oligomer is that obtained from cyanoacrylates which in situ form a cyanoacrylate polymer on the skin surface.

Such use of cyanoacrylate polymers per this invention is in contrast to their known medical uses as an alternative or adjunct to sutures[7] or as a hemostat[8]. Other described uses of cyanoacrylate polymers include their use to prevent friction blister formation[4]; to inhibit pressure ulcer formation[11], to form a barrier layer in the treatment of incontinences[5]; to treat small non-suturable wounds[9]; and to inhibit surface skin irritation arising from friction between the skin surface and artificial devices such as tapes, prosthetic devices, casts, and the like.[10]

SUMMARY OF THE INVENTION

This invention is directed to methods for inhibiting late radiation-induced skin damage arising after treatment of a patient with ionizing radiation by covering the skin during radiation exposure with a biocompatible polymer layer.

Accordingly, in one of its method aspects, this invention is directed to a method for inhibiting late radiation-induced skin damage to a human patient arising after treatment of that patient with ionizing radiation wherein application of radiation was through a portion of the skin thereby exposing the epidermal layer of that skin portion to said ionizing radiation which method comprises:

(a) applying a layer of biocompatible polymer of no more than 1 millimeter in thickness to the surface of the skin area which is to be exposed to ionizing radiation; and (b) exposing the patient to ionizing radiation through the layer of biocompatible polymer.

Application of the layer of biocompatible polymer is preferably made onto the surface of intact skin. More preferably, the intact skin is further characterized as lacking any infection, open wounds, etc. which would permit the polymer to penetrate from the surface of the epidermis to or beyond the dermal layer.

In one preferred embodiment, the layer of biocompatible polymer is formed on the skin surface by solvent casting. In this embodiment, a suitable biocompatible polymer is dissolved or dispersed in a biocompatible solvent and applied onto the surface of the skin. Upon dissipation of the solvent, a thin polymer layer forms on the skin surface.

In another preferred embodiment, the layer of biocompatible polymer is formed by the in situ polymerization of a reactive monomer or oligomer (prepolymer) on the skin surface. Suitable reactive monomers and oligomers include, by way of example, cyanoacrylates, urethanes, silicones and the like. Preferred reactive monomers and oligomers are cyanoacrylates and, particularly, n-butyl cyanoacrylate.

In this preferred embodiment, this invention is directed to a method for inhibiting late radiation-induced skin damage to a human patient arising from treatment of that patient with ionizing radiation wherein application of the radiation is through a portion of the skin thereby exposing the epidermal layer of that skin portion to said ionizing radiation which method comprises:

(a) applying a layer of cyanoacrylate polymer of no more than 1 millimeter in thickness to the surface of the skin area which is to be exposed to ionizing radiation; and (b) exposing the patient to ionizing radiation through the layer of cyanoacrylate polymer.

In a further preferred embodiment, the cyanoacrylate, in monomeric form, is represented by formula I:

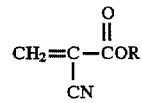

I where R is selected from the group consisting of:
alkyl of 2 to 10 carbon atoms,
alkenyl of 2 to 10 carbon atoms,
cycloalkyl groups of from 5 to 8 carbon atoms, phenyl,
2-ethoxyethyl,
3-methoxybutyl,
and a substituent of the formula:

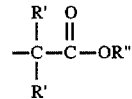

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

In still another of its method aspects, this invention is directed to a method for inhibiting late radiation-induced skin damage to a human patient during treatment of that patient with ionizing radiation wherein application of the radiation is through a portion of the skin thereby exposing the epidermal layer of that skin portion to said ionizing radiation which method comprises:

(a) applying to skin surface area(s) which will be exposed to ionizing radiation a sufficient amount of a cyanoacrylate adhesive so as to cover said area(s);

(b) polymerizing the cyanoacrylate adhesive so as to form a flexible, waterproof, adhesive polymer layer of no more than 1 millimeter in thickness which adheres to the area(s) where the adhesive was applied; and (c) exposing the patient to ionizing radiation through the layer of cyanoacrylate polymer wherein the cyanoacrylate adhesive, in monomeric form, is represented by formula I above.

Preferably, in the cyanoacrylates of formula I, R is alkyl of from 2 to 10 carbon atoms and more preferably alkyl of from 2 to 8 carbon atoms. Even more preferably, R is butyl, pentyl or octyl and most preferably, R is n-butyl.

The biocompatible polymer layer has a thickness of no more than about 1 millimeter so as to avoid a bolus affect on the skin which would exacerbate the skin damage induced by the radiation. More preferably, the biocompatible polymer has a thickness of from about 0.1 to about 0.5 millimeters and still more preferably from about 0.3 to about 0.5 millimeters.

DETAILED DESCRIPTION OF THE PREFERRED EMBODIMENTS

This invention relates to methods for inhibiting late radiation-induced skin damage arising from treatment of a patient with ionizing radiation. However, prior to discussing this invention in further detail, the following terms will first be defined.

Definitions

As used herein, the following terms have the following meanings:

The term "ionizing radiation" refers to radiation commonly employed in the treatment of tumors (whether benign or cancerous) which radiation, either as a large single dosage or as repeated smaller dosages, will cause acute and/or late skin damage in at least a portion of the patients exposed to this dosage of radiation. Ionizing radiation includes, by way of example, x-rays, electron beams, γ-rays, and the like.

The term "acute radiation-induced skin damage" refers to the damage to the epidermal layer of the skin caused by either a single large dosage or repeated smaller dosages of ionizing radiation which damage can manifest itself about 3-5 weeks after treatment with ionizing radiation. Acute radiation-induced skin damage is sometimes referred to as early radiation induced skin damage and includes, by way of example, erythema, dry desquamation, moist desquamation, epilation and ulceration. Acute radiation-induced skin damage can be particularly severe in skin folds and areas of high friction, e.g., groin, buttocks, the folds of the breast, neck, etc. and the like.

The term "late radiation-induced skin damage" refers to skin damage arising 6 or more months after termination of the radiation treatment which damage includes, by way of example, atrophy, fibrosis, thinning, telangiectasia, altered pigmentation, ulceration, necrosis and carcinogenesis.

The term "biocompatible polymer" refers to a polymer which can form a water-insoluble polymeric layer over the skin, which is compatible with the skin as measured by the lack of skin irritation and which can be removed from the skin by conventional means, e.g., sloughing off with the epidermal layer. Preferably, the polymer has a number average molecular weight of at least about 10,000, more preferably from about 10,000 to about 500,000 and still more preferably from about 50,000 to about 250,000. Suitable biocompatible polymers are well known in the art and include, by way of example, cyanoacrylate polymers, cellulosics, polyurethane, poly($C_1$-$C_6$alkyl)methacrylate, polyhydroxyalkyl acrylates, polyhydroxyalkyl alkacrylates (e.g., HEMA—polyhydroxyethyl methacrylate), polyesters, and the like, as well as mixtures and copolymers thereof including the butyl ester of polyvinyl alcohol and maleic arthydride copolymer, mixtures of 1:1 n-butyl & iso-butyl methacrylate, and the like. Biocompatible polymers are also found in conventional skin care products such as Smith & Nephew Skin Prep™, Mentor Shield Skin™, Bard™ & Allkare™ Protective Barrier, and 3M™ No Sting Barrier Film, as disclosed by Lutz, in *Performance Assessment of Film Forming Skin Protectants (Sealants)*.

The term "cyanoacrylate adhesive" refers to polymerizable adhesive formulations comprising cyanoacrylate monomers or polymerizable oligomers which in their monomer form are compounds represented by formula I as described above.

Preferably, in formula I, R is an alkyl group of from 2 to 10 carbon atoms including ethyl, n-propyl, iso-propyl, n-butyl, iso-butyl, sec-butyl, n-pentyl, iso-pentyl, n-hexyl, iso-hexyl, 2-ethylhexyl, n-heptyl, octyl, nonyl, and decyl. More preferably, R is butyl, pentyl or octyl and most preferably, R is n-butyl.

These cyanoacrylate adhesives are known in the art and are described in, for example, U.S. Pat. Nos. 3,527,224; 3,591,676; 3,667,472; 3,995,641; 4,035,334; and 4,650,826 the disclosures of each are incorporated herein by reference in their entirety.

A preferred cyanoacrylate adhesive for use in the invention is n-butyl-2-cyanoacrylate.

The cyanoacrylate adhesives described herein rapidly polymerize in the presence of water vapor or tissue protein, and the n-butyl-cyanoacrylate is capable of bonding human skin tissue without causing histotoxicity or cytotoxicity.

The term "biocompatible plasticizer" refers to any material which is soluble or dispersible in the prepolymer or polymer composition, which increases the flexibility of the resulting polymer coating on the skin surface, and which is compatible with the skin as measured by the lack of skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate, butyl benzyl phthalate, dibutyl phthalate, diethyl phthalate, dimethyl phthalate, dioctylphthalate, n-butyryl tri-n-hexyl citrate, benzoate esters of di- and poly-hydroxy branched aliphatic compounds, tri(p-cresyl) phosphate, and the like. The particular plasticizer employed is not critical and preferred plasticizers include alkyl phthalates independently having from 1 to 10 carbon atoms in each alkyl group. A particularly preferred plasticizer is dioctylphthalate.

The term "biocompatible solvent" refers to those solvents or mixture of solvents which dissolve or disperse the biocompatible polymer, which dissipate from the skin upon application, and which are compatible with the skin as measured by the lack of skin irritation. Examples of suitable biocompatible solvents include, by way of example only, DMSO, acetone, ethanol, isopropanol, hexamethyl disiloxane, etc.

Methods

The methods of this invention comprise application of a layer of a biocompatible polymer onto surface skin areas prior to exposure to ionizing radiation. The biocompatible polymer layer or coating can be applied onto the skin surface as a polymer solution or as prepolymeric formulation comprising polymerizable monomers and oligomers. Preferably, the skin area is clean and dry prior to application of the polymer layer.

When a polymer solution is employed, a requisite amount of the solution or dispersion of the polymer in a biocompatible solvent is applied to the skin surface and, upon dissipation of the solvent, a waterproof layer of polymer is formed thereon. In this embodiment, the thickness of the polymer layer is controlled by the concentration of the polymer in solution and the amount of solution applied to the skin. Such factors are well within the skill of the art.

Dissipation of the biocompatible solvent is achieved typically by evaporation upon contact with the skin and, accordingly, low boiling point solvents (b.p. <~100° C.) are preferred for this purpose. Dissipation can also be achieved by bioabsorption of the solvent across the skin barrier such as in the case of DMSO. The particular method for dissipating the solvent is not critical.

In a preferred embodiment, the solution can further comprise a biocompafible plasticizer and other optional additives. Typically, the solution will comprise from about 1 to about 10 weight percent of a biocompatible polymer based on the total weight of the solution.

More preferably, a prepolymeric formulation comprising polymerizable monomers and/or oligomers is employed. Upon application of the monomers and/or oligomers to the skin, polymerization occurs. Such polymerization can be initiated by, for example, surface skin moisture, tissue protein, etc. Alternatively, a conventional polymerization initiator can be included just prior to application of the prepolymeric formulation to the skin. Thereafter, the skin surface is maintained under suitable conditions to allow polymerization to proceed to formation of the polymer layer. In general, the particular length of time required for polymerization will vary depending on factors such as the amount and type of prepolymer formulation applied, the surface area of skin to which the adhesive was applied, and the like. However, in a preferred embodiment, polymerization is generally complete within about 10 to about 60 seconds while the skin is maintained at ambient conditions. During this period, the person to whom application of the prepolymeric formulation has been made merely allows the formulation to form a polymer layer while minimizing any action to prevent the formulation from being dislodged from that portion of the skin where it was applied or to adhere to unintended objects.

A particularly preferred prepolymer is a composition comprising a cyanoacrylate prepolymer ("adhesive") which, upon application to the skin, the surface skin moisture, tissue protein, and temperature are sufficient to initiate polymerization of the adhesive upon application. Thereafter, the skin surface is maintained under suitable conditions to allow polymerization to proceed to formation of the polymer layer. As before, the particular length of time required for polymerization will vary depending on factors such as the amount of adhesive applied, the temperature of the skin, the moisture content of the skin, the surface area of skin to which the adhesive was applied, and the like. However, in a preferred embodiment, polymerization is generally complete within about 10 to about 60 seconds while the skin is maintained at ambient conditions. During this period, the person to whom application of the cyanoacrylate adhesive has been made merely allows the adhesive to form a polymer layer while minimizing any action to prevent the adhesive from being dislodged from that portion of the skin where it was applied or to adhere to unintended objects.

Whether the polymer layer is formed from a solution comprising the polymer or by in situ polymerization of a prepolymer on the skin surface, sufficient amounts of applied composition are employed to cover (i.e., coat) the entire surface skin area to be exposed to ionizing radiation with a layer of the cyanoacrylate polymer. The specific manner of application and location of the polymer layer is typically determined by the radiation oncologist or other health care professionals. Preferably, the layer is extended beyond the area to be exposed by at least about 1 centimeter and more preferably by at least about 5 centimeters. When the polymer is cyanoacrylate, excess polymer can be removed with acetone (nail polish remover) which can be readily conducted except in the case where the adhesive polymer binds to a sensitive skin part (e.g., the eye lids) where it should be removed by a health care professional.

After formation of the polymer layer on the surface of the skin, the polymer adheres to the skin, is flexible and waterproof, thereby forming a protective coating which enhances the integrity of the underlying skin. Adherence to the skin is enhanced by in situ formation of the polymer layer preferably from a cyanoacrylate adhesive.

While not being limited to any theory, we believe that the polymer layer inhibits late radiation-induced skin damage by inhibiting skin damage during radiation treatment. In turn, inhibition of radiation-induced skin damage occurs by minimizing moisture loss to the covered skin areas; by preventing frictional contact of the covered skin with, for example, clothing; and by enhancing the underlying skin integrity. By inhibiting initial skin damage, further and more acute skin damage due to the inflammatory response of the initial skin damage is prevented.

In general, the polymer layer will adhere to the skin for a period of about 2-4 days after which time it sloughs off. Accordingly, the polymer layer need not be removed in the manner of other adhesives/dressings whose removal results in skin irritation.

The polymer layer is formed over the skin surface prior to exposure of that surface with ionizing radiation. Preferably, the polymer layer is maintained during periods between radiation exposure merely by reapplication of the layer as necessary in the manner described above. In a particularly preferred embodiment, the polymer layer is maintained continuously throughout the period of ionizing radiation treatment and up to 4 weeks after treatment termination. Preferably, prior to reapplication of the polymer layer to the skin, the skin surface is again cleaned.

The polymer layer should be maintained in a unbroken manner over the entire skin area to be exposed to ionizing radiation. This can be assured by careful application of the polymer (either as a polymer solution or as the polymerizable monomer or oligomer) onto the skin. Additionally, the use of a plasticizer will facilitate the maintenance of the polymer coating in an unbroken manner.

In a preferred embodiment, after application of the initial polymer layer, a second, preferably thinner, layer is applied over the coating. Additional amounts of polymer solution or the prepolymer can be applied as needed to maintain an unbroken coating covering over the surface skin areas.

Application is conducted under conditions wherein the polymer layer has a thickness of no more than about 1 millimeter and preferably has a thickness of from about 0.1 to about 0.5 millimeters. Such a thickness will ensure that the polymer does not act in the manner of a bolus. The amount of polymer solution or prepolymer applied to obtain this thickness is well within the skill of the art.

The polymer layer applied onto the skin surface area can be readily controlled by the amount of polymer solution or prepolymer packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is particularly advantageous because it dispenses the prepolymer or polymer solution in a controlled dropwise manner. Other methods for the controlled dispersement include, by way of example, a spray applicator, a brush or solid paddle applicator, applicators for repeated and intermittent use of the cyanoacrylate composition and the like.

A preferred applicator for repeated and intermittent usage is an applicator suitable for the non-sterile storage and metered dispersement of the composition after opening of the applicator wherein the applicator is characterized as having a resealable opening of no more than about 0.008 square inches (0.0516 square centimeters) so as to permit the metered dispersement of the composition from the applicator and which is capable of multiple administrations of the composition and is further characterized as having reseating means such as a cap which either tightly mates with the applicator or which screws onto the applicator.

Preferably, the opening of the applicator is about 0.0016 to about 0.003 square inches (about 0.0103 to about 0.0194 square centimeters).

In another preferred embodiment, the walls of the applicator are made of a pliable material, so that upon application of pressure onto the walls, the walls depress sufficiently to force the composition contained in the applicator through the opening. Preferably, the applicator is manufactured with its opening covered by a metal foil or other similar construction which closes this opening until the device is ready for use. The opening is then reinstated by use of a pin or similar device which punctures the covering.

When a cyanoacrylate prepolymer composition is employed in applicators suitable for repeated intermittent uses, the alkyl cyanoacrylate composition is stored at ambient conditions and can be selected to be bacteriostatic. See, for example, Rabinowitz et al., U.S. Pat. No. 3,527,224. When the selected composition is bacteriostatic, prolonged storage at ambient conditions is without regard to the sterility of the formulation because there is no adverse buildup of bacteria during storage.

Because the polymer layer is waterproof, the patient is not prevented from bathing and other activities involving exposure to water during the period the polymer layer protects this skin area.

Compositions

The polymer or prepolymer compositions described herein are prepared by conventional methods of mixing the appropriate components until homogenous.

The specific viscosity of these prepolymer and polymer compositions depends, in part, on the intended application of the composition. For example, relatively low viscosities are often preferred where application is to be made to a large surface area. This preference results from the fact that those forms are less viscous and, accordingly, will permit more facile large surface area application of a thin application. Contrarily, where application is to be made to a specific position on the skin, higher viscosity materials are preferred to prevent "running" of the material to unintended locations.

Accordingly, these compositions have a viscosity of from about 2 to 50,000 centipoise at 20° C. Preferably from about 2 to 1,500 centipoise at 20° C. More preferably, when a prepolymer is employed, the prepolymer is almost entirely in monomeric form and the composition has a viscosity of from about 5 to about 100 centipoise at 20° C.

A thickening agent is optionally employed to increase the viscosity of the composition which thickening agent is any biocompatible material which increases the viscosity of the composition whether as a prepolymer composition or as a polymeric composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000. Suitable thickening agents for prepolymeric compositions also include a partial polymer of the alkyl cyanoacrylate as disclosed in U.S. Pat. Nos. 3,654,239 and 4,038,345 both of which are incorporated herein by reference in their entirety.

Thickening agents are deemed to be biocompatible if they are both soluble or dispersible in the composition and are compatible with the skin as measured by the lack of skin irritation.

The prepolymer and polymer compositions preferably include a biocompatible plasticizer and such plasticizers are preferably included from about 10 to 30 weight percent and more preferably from about 18 to 25 weight percent based on the weight of the composition in the absence of any solvent.

Additionally, in prepolymeric compositions such as cyanoacrylate prepolymers, a polymerization inhibitor is also preferably employed and, in a particularly preferred embodiment, this inhibitor is sulfur dioxide which is employed at from about 50 to 500 ppm based on the total weight of the composition.

The prepolymer and polymer compositions may additionally contain one or more optional additives such as colorants, perfumes, anti-diffusion agents, rubber modifiers, modifying agents, etc. In practice, each of these optional additives should be both miscible and compatible with the prepolymer and the polymer. Compatible additives are those that do not prevent the use of the prepolymers and the polymers in the manner described herein.

In general, colorants are added so that the polymer layer formed on the skin will contain a discrete and discernable color. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate compositions useful in the practice of this invention are also disclosed by Greff, et al., U.S. Pat. No. 5,480,935, which application is incorporated herein by reference in its entirety.

Utility

The methods described herein are useful in inhibiting late radiation-induced skin damage during radiation treatment of malignant and benign tumors. Such tumors include, by way of example only, tumors associated with breast cancer, tumors associated with prostate cancer, tumors associated with rectal cancer, brain tumors, tumors associated with lymph node cancer, and any other tumors where ionizing radiation forms a part of the treatment regimen.

These methods are particularly useful in prophylactic methods to inhibit the late effects of skin damage due to radiation treatment by either reducing the severity of the skin damage and/or by delaying the onset of the damage.

The following example illustrates certain embodiments of the invention but is not meant to limit the scope of the claims in any way.

EXAMPLE

Several cancer patients were evaluated to compare the effect on late radiation-induced skin damage during radiation therapy.

In this example, each of the patients applied a cyanoacrylate adhesive composition comprising n-butyl α-cyanoacrylate in monomeric form, 20 weight percent of dioctyl phthalate as a plasticizer and 200 ppm $SO_2$ over the entire area to be exposed to radiation. The composition was then allowed to polymerize whereby a polymer layer was formed. Application of this composition was conducted prophylactically on day 1 and every other day during radiation treatment and for up to 4 weeks post therapy. Radiation therapy was delivered using standard fractionation techniques to total doses of 50–60 Gy.

After 6 months, the patients were evaluated by the nurse or physician to score the late effects of radiation-induced skin damage. One method for evaluating such late skin effects include those using the Radiation Therapy Oncology Group (RTOG), Reston, Va., USA, where the late effects of radiation-induced skin damage is measured as set forth in the following table:

| LATE EFFECTS ON RADIATION INDUCED SKIN DAMAGE GRADING SCALE | |
| --- | --- |
| GRADE | SKIN CHARACTERISTICS |
| 0 | None |
| 1 | Slight atrophy; pigmentation change; some hair loss. |
| 2 | Patch atrophy; moderate telangiectasia; total hair loss |
| 3 | Marked atrophy; gross telangiectasia |
| 4 | Ulceration |

From this evaluation, the patients were not identified as showing any late effects of radiation-induced skin damage.

From the foregoing description, various modifications and changes in the composition and method will occur to those skilled in the art. All such modifications coming within the scope of the appended claims are intended to be included therein.

What is claimed is:

1. A method for inhibiting late radiation-induced skin damage to a patient arising from treatment of that patient with ionizing radiation wherein application of the radiation is through a portion of the skin thereby exposing the epidermal layer of that skin portion to said ionizing radiation which method comprises:
   (a) applying a layer of biocompatible polymer of no more than 1 millimeter in thickness to the surface of the skin area which is to be exposed to ionizing radiation; and
   (b) exposing the patient to ionizing radiation through the layer of biocompatible polymer.

2. The method according to claim 1 wherein the treatment comprises exposing the patient to ionizing radiation up to 5 times per week over 4–10 weeks.

3. The method according to claim 1 wherein said layer of biocompatible polymer is maintained over the skin throughout the entire treatment period.

4. The method according to claim 3 wherein said layer of biocompatible polymer is maintained over the skin for up to 4 weeks after exposure to ionizing radiation terminates.

5. The method according to claim 1 wherein said biocompatible polymer is applied onto the intact skin surface as a prepolymer which polymerizes in situ to provide for the layer of biocompatible polymer.

6. The method according to claim 5 wherein said biocompatible polymer is applied onto the intact skin surface as a polymer solution comprising a biocompatible solvent and the biocompatible polymer which is either dissolved or dispersed therein and the biocompatible solvent is permitted to dissipate from the skin surface leaving a polymer layer thereon.

7. The method according to claim 1 wherein said polymer further comprises a biocompatible plasticizer.

8. The method according to claim 7 wherein said biocompatible plasticizer is dioctyl phthalate.

9. The method according to claim 5 wherein the prepolymer further comprises a polymerization inhibitor.

10. The method according to claim 9 wherein said polymerization inhibitor is $SO_2$.

11. The method according to claim 1 wherein the polymer layer has a thickness of from about 0.1 to about 0.5 millimeters.

12. A method for inhibiting late radiation-induced skin damage to a patient arising from treatment of that patient with ionizing radiation wherein application of the radiation is through a portion of the skin thereby exposing the epidermal layer of that skin portion to said ionizing radiation which method comprises:
   (a) applying to skin surface area(s) which will be exposed to ionizing radiation a sufficient amount of a prepolymer composition so as to cover said area(s);
   (b) polymerizing the prepolymer so as to form a flexible, waterproof, adhesive polymer layer having a thickness of no more than 1 millimeter which adheres to the area(s) where the adhesive was applied; and
   (c) exposing the patient to ionizing radiation through the layer of polymer layer.

13. The method according to claim 12 wherein the treatment comprises exposing the patient to ionizing radiation up to 5 times per week over 4–10 weeks.

14. The method according to claim 12 wherein said layer of polymer is maintained over the skin throughout the entire treatment period.

15. The method according to claim 14 wherein said layer of polymer is maintained over the skin for up to 4 weeks after exposure to ionizing radiation terminates.

16. The method according to claim 12 wherein said polymer comprises a biocompatible plasticizer.

17. The method according to claim 16 wherein said biocompatible plasticizer is dioctyl phthalate.

18. The method according to claim 16, wherein the prepolymer further comprises a polymerization inhibitor.

19. The method according to claim 18 wherein said polymerization inhibitor is $SO_2$.

20. The method according to claim 12 wherein the polymer layer has a thickness of from about 0.1 to about 0.5 millimeters.

21. A method for inhibiting late radiation-induced skin damage to a patient arising from treatment of that patient with ionizing radiation wherein application of the radiation is through a portion of the skin thereby exposing the epidermal layer of that skin portion to said ionizing radiation which method comprises:
   (a) applying a layer of cyanoacrylate polymer having a thickness of no more than 1 millimeter to the surface of the skin area which is to be exposed to ionizing radiation; and
   (b) exposing the patient to ionizing radiation through the layer of cyanoacrylate polymer.

22. The method according to claim 21 wherein the treatment comprises exposing the patient to ionizing radiation up to 5 times per week over 4–10 weeks.

23. The method according to claim 21 wherein said layer of cyanoacrylate polymer is maintained over the skin throughout the entire treatment period.

24. The method according to claim 23 wherein said layer of cyanoacrylate polymer is maintained over the skin for up to 4 weeks after exposure to ionizing radiation terminates.

25. The method according to claim 21 wherein said cyanoacrylate polymer, in monomeric form, is selected from the group consisting of octyl cyanoacrylate and butyl cyanoacrylate.

26. The method according to claim 25 wherein said cyanoacrylate polymer, in monomer form, is n-butyl cyanoacrylate.

27. The method according to claim 21 wherein said polymer further comprises a biocompatible plasticizer.

28. The method according to claim 27 wherein said biocompatible plasticizer is dioctyl phthalate.

29. The method according to claim 25 wherein said polymer still further comprises a polymerization inhibitor.

30. The method according to claim 29 wherein said polymerization inhibitor is $SO_2$.

31. The method according to claim 30 wherein the polymer layer has a thickness of from about 0.1 to about 0.5 millimeters.

* * * * *